US010525171B2

(12) United States Patent
Ruane et al.

(10) Patent No.: US 10,525,171 B2
(45) Date of Patent: Jan. 7, 2020

(54) COATINGS FOR MEDICAL DEVICES

(71) Applicant: The Spectranetics Corporation, Colorado Springs, CO (US)

(72) Inventors: Patrick Ruane, Redwood City, CA (US); Cameron Wilson, Moss Beach, CA (US); Steven Ummel, Menlo Park, CA (US); Arlene Alcantara, San Jose, CA (US); Jackie Joe Hancock, Cork (IE); Qi Zhan, Antioch, CA (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 1465 days.

(21) Appl. No.: 14/162,900

(22) Filed: Jan. 24, 2014

(65) Prior Publication Data
US 2015/0209555 A1    Jul. 30, 2015

(51) Int. Cl.
*A61L 29/16* (2006.01)
*A61M 25/10* (2013.01)
(Continued)

(52) U.S. Cl.
CPC ............. *A61L 29/16* (2013.01); *A61L 29/085* (2013.01); *A61M 25/10* (2013.01); *C08L 71/02* (2013.01);
(Continued)

(58) Field of Classification Search
CPC .... A61L 29/085; A61L 29/16; A61L 2420/06; A61L 2300/416; A61L 2300/106; A61M 25/10
See application file for complete search history.

(56) References Cited

U.S. PATENT DOCUMENTS 4,010,259 A    3/1977  Johansson
4,589,873 A    5/1986  Schwartz et al.
(Continued)

FOREIGN PATENT DOCUMENTS

EP    0706376 A1    4/1996
EP    0797988 A2    10/1997
(Continued)

OTHER PUBLICATIONS

Examiner's First Report issued in Australian Application No. 2013280330 dated Dec. 24, 2014.
(Continued)

*Primary Examiner* — Nathan R Price
*Assistant Examiner* — Melissa A Snyder

(57) ABSTRACT

A method and device for local delivery of a water-insoluble therapeutic agent to the tissue of a normal or diseased body lumen is disclosed. An expandable structure of a medical disposable device, such as a balloon of a balloon catheter, is coated with a non-durable coating which includes an amphiphilic polymer or copolymer, in embodiments polyethylene glycol, having a substantially water-insoluble therapeutic agent dispersed therein. In some embodiments, the coating may also include iodine. The medical disposable device is inserted into a body lumen, and expanded to contact the non-durable coating against the body lumen and deliver the substantially water-insoluble therapeutic agent to the body lumen tissue.

17 Claims, 6 Drawing Sheets

(51) Int. Cl.
*A61L 29/08* (2006.01)
*C08L 71/02* (2006.01)

(52) U.S. Cl.
CPC ... *A61L 2300/106* (2013.01); *A61L 2300/416* (2013.01); *A61L 2420/06* (2013.01); *A61M 25/1002* (2013.01); *A61M 2025/105* (2013.01); *A61M 2025/1075* (2013.01)

(56) References Cited

U.S. PATENT DOCUMENTS

| | | |
|---|---|---|
| 4,847,324 A | 7/1989 | Creasy |
| 4,950,256 A | 8/1990 | Luther et al. |
| 5,001,009 A | 3/1991 | Whitbourne |
| 5,256,701 A | 10/1993 | Tamura et al. |
| 5,302,392 A | 4/1994 | Karakelle et al. |
| 5,302,394 A | 4/1994 | Beahm |
| 5,304,121 A | 4/1994 | Sahatjian |
| 5,331,027 A | 7/1994 | Whitbourne |
| 5,464,650 A | 11/1995 | Berg et al. |
| 5,525,348 A | 6/1996 | Whitbourne et al. |
| 5,570,475 A | 11/1996 | Nile et al. |
| 5,616,608 A | 4/1997 | Kinsella et al. |
| 5,662,609 A | 9/1997 | Slepian |
| 5,674,192 A | 10/1997 | Sahatjian et al. |
| 5,733,888 A | 3/1998 | Carver et al. |
| 5,733,925 A | 3/1998 | Kunz et al. |
| 5,762,638 A | 6/1998 | Shikani et al. |
| 5,766,192 A | 6/1998 | Zacca |
| 5,788,979 A | 8/1998 | Alt et al. |
| 5,811,447 A | 9/1998 | Kunz et al. |
| 5,824,049 A | 10/1998 | Ragheb et al. |
| 5,886,026 A | 3/1999 | Hunter et al. |
| 5,900,246 A | 5/1999 | Lambert |
| 5,954,706 A | 9/1999 | Sahatjian |
| 5,972,992 A | 10/1999 | Carver et al. |
| 5,977,164 A | 11/1999 | Carver et al. |
| 6,074,659 A | 6/2000 | Kunz et al. |
| 6,096,070 A | 8/2000 | Ragheb et al. |
| 6,096,331 A | 8/2000 | Desai et al. |
| 6,110,483 A | 8/2000 | Whitbourne et al. |
| 6,120,784 A | 9/2000 | Snyder, Jr. |
| 6,146,358 A | 11/2000 | Rowe |
| 6,156,373 A | 12/2000 | Zhong et al. |
| 6,179,817 B1 | 1/2001 | Zhong |
| 6,218,016 B1 | 4/2001 | Tedeschi et al. |
| 6,268,390 B1 | 7/2001 | Kunz |
| 6,299,604 B1 | 10/2001 | Ragheb et al. |
| 6,306,166 B1 | 10/2001 | Barry et al. |
| 6,306,421 B1 | 10/2001 | Kunz et al. |
| 6,369,039 B1 | 4/2002 | Palasis et al. |
| 6,403,635 B1 | 6/2002 | Kinsella et al. |
| 6,419,692 B1 | 7/2002 | Yang et al. |
| 6,429,232 B1 | 8/2002 | Kinsella et al. |
| 6,506,408 B1 | 1/2003 | Palasis |
| 6,506,411 B2 | 1/2003 | Hunter et al. |
| 6,515,009 B1 | 2/2003 | Kunz et al. |
| 6,537,579 B1 | 3/2003 | Desai et al. |
| 6,544,544 B2 | 4/2003 | Hunter et al. |
| 6,638,767 B2 | 10/2003 | Unger et al. |
| 6,663,881 B2 | 12/2003 | Kunz et al. |
| 6,673,053 B2 | 1/2004 | Wang et al. |
| 6,730,064 B2 | 5/2004 | Ragheb et al. |
| 6,753,071 B1 | 6/2004 | Pacetti |
| 6,774,278 B1 | 8/2004 | Ragheb et al. |
| 6,835,387 B2 | 12/2004 | Herrmann |
| 6,846,815 B2 | 1/2005 | Myers et al. |
| 6,855,770 B2 | 2/2005 | Pinchuk et al. |
| 6,918,927 B2 | 7/2005 | Bates et al. |
| 6,926,919 B1 | 8/2005 | Hossainy et al. |
| 7,008,979 B2 | 3/2006 | Schottman et al. |
| 7,105,175 B2 | 9/2006 | Schwarz |
| 7,179,251 B2 | 2/2007 | Palasis |
| 7,279,174 B2 | 10/2007 | Pacetti et al. |
| 7,291,165 B2 | 11/2007 | Rosenthal et al. |
| 7,381,418 B2 | 6/2008 | Richard |
| 7,407,507 B2 | 8/2008 | Maeda et al. |
| 7,445,792 B2 | 11/2008 | Toner et al. |
| 7,482,034 B2 | 1/2009 | Boulais |
| 7,541,047 B2 | 6/2009 | Rogasch et al. |
| 7,750,041 B2 | 7/2010 | Speck et al. |
| 7,803,149 B2 | 9/2010 | Bates et al. |
| 7,811,622 B2 | 10/2010 | Bates et al. |
| 7,875,284 B2 | 1/2011 | Reyes et al. |
| 7,914,806 B2 | 3/2011 | Strickler et al. |
| 7,919,108 B2 | 4/2011 | Reyes et al. |
| 8,021,678 B2 | 9/2011 | Hossainy et al. |
| 8,114,429 B2 | 2/2012 | Michal et al. |
| 8,128,951 B2 | 3/2012 | Michal et al. |
| 8,147,540 B2 | 4/2012 | Reyes et al. |
| 8,257,305 B2 | 9/2012 | Speck et al. |
| 8,257,722 B2 | 9/2012 | Michal et al. |
| 8,313,521 B2 | 11/2012 | Ruane et al. |
| 8,389,043 B2 | 3/2013 | Speck et al. |
| 8,439,868 B2 | 5/2013 | Speck et al. |
| 8,491,925 B2 | 7/2013 | Michal et al. |
| 2002/0151844 A1 | 10/2002 | Yang et al. |
| 2003/0052424 A1 | 3/2003 | Turner et al. |
| 2003/0059454 A1 | 3/2003 | Barry et al. |
| 2003/0203991 A1 | 10/2003 | Schottman et al. |
| 2003/0225451 A1 | 12/2003 | Sundar |
| 2004/0073284 A1 | 4/2004 | Bates et al. |
| 2004/0117006 A1 | 6/2004 | Lewis et al. |
| 2004/0117007 A1 | 6/2004 | Whitbourne et al. |
| 2004/0175406 A1 | 9/2004 | Schwarz |
| 2004/0230298 A1* | 11/2004 | Udipi ............... A61F 2/82 623/1.42 |
| 2004/0241094 A1 | 12/2004 | Chung et al. |
| 2005/0004661 A1 | 1/2005 | Lewis et al. |
| 2005/0036946 A1 | 2/2005 | Pathak et al. |
| 2005/0059965 A1 | 3/2005 | Eberl et al. |
| 2005/0113510 A1 | 5/2005 | Feldstein et al. |
| 2005/0147690 A1 | 7/2005 | Masters et al. |
| 2005/0159704 A1 | 7/2005 | Scott et al. |
| 2005/0226903 A1 | 10/2005 | Rogasch et al. |
| 2005/0250672 A9 | 11/2005 | Speck et al. |
| 2005/0278021 A1 | 12/2005 | Bates et al. |
| 2006/0020243 A1 | 1/2006 | Speck et al. |
| 2006/0020331 A1 | 1/2006 | Bates et al. |
| 2006/0034769 A1 | 2/2006 | Kohn et al. |
| 2006/0212106 A1 | 9/2006 | Weber et al. |
| 2006/0228453 A1 | 10/2006 | Cromack et al. |
| 2006/0240070 A1 | 10/2006 | Cromack et al. |
| 2007/0065481 A1 | 3/2007 | Chudzik et al. |
| 2007/0065482 A1 | 3/2007 | Chudzik et al. |
| 2007/0065483 A1 | 3/2007 | Chudzik et al. |
| 2007/0065484 A1 | 3/2007 | Chudzik et al. |
| 2007/0071792 A1 | 3/2007 | Varner et al. |
| 2007/0078446 A1 | 4/2007 | Lavelle |
| 2007/0104766 A1 | 5/2007 | Wang et al. |
| 2007/0190103 A1 | 8/2007 | Hossainy et al. |
| 2008/0020013 A1 | 1/2008 | Reyes et al. |
| 2008/0021385 A1 | 1/2008 | Barry et al. |
| 2008/0051871 A1 | 2/2008 | Tuch |
| 2008/0078400 A1 | 4/2008 | Martens et al. |
| 2008/0102033 A1 | 5/2008 | Speck et al. |
| 2008/0102034 A1 | 5/2008 | Speck et al. |
| 2008/0113035 A1 | 5/2008 | Hunter |
| 2008/0118543 A1 | 5/2008 | Pacetti et al. |
| 2008/0118544 A1 | 5/2008 | Wang |
| 2008/0124372 A1 | 5/2008 | Hossainy et al. |
| 2008/0132992 A1 | 6/2008 | Bates et al. |
| 2008/0140002 A1 | 6/2008 | Ramzipoor et al. |
| 2008/0145396 A1 | 6/2008 | Bates et al. |
| 2008/0146489 A1 | 6/2008 | Pacetti et al. |
| 2008/0153900 A1 | 6/2008 | Hunter |
| 2008/0175887 A1 | 7/2008 | Wang |
| 2008/0311173 A1 | 12/2008 | Schwarz et al. |
| 2009/0054837 A1 | 2/2009 | Von Holst et al. |
| 2009/0074707 A1 | 3/2009 | Rogasch et al. |
| 2009/0098176 A1 | 4/2009 | Helmus et al. |
| 2009/0112239 A1 | 4/2009 | To |
| 2009/0136560 A1 | 5/2009 | Bates et al. |
| 2009/0186414 A1 | 7/2009 | Srivastava et al. |

(56) References Cited

U.S. PATENT DOCUMENTS

| | | | |
|---|---|---|---|
| 2009/0196931 A1 | 8/2009 | Kunz et al. | |
| 2009/0216317 A1 | 8/2009 | Cromack et al. | |
| 2009/0218731 A1 | 9/2009 | Rogasch et al. | |
| 2009/0227948 A1 | 9/2009 | Chen et al. | |
| 2009/0227949 A1 | 9/2009 | Knapp et al. | |
| 2009/0285974 A1 | 11/2009 | Kerrigan et al. | |
| 2009/0297584 A1 | 12/2009 | Lim et al. | |
| 2010/0015200 A1 | 1/2010 | McClain et al. | |
| 2010/0030183 A1 | 2/2010 | Toner et al. | |
| 2010/0063570 A1 | 3/2010 | Pacetti et al. | |
| 2010/0063585 A1 | 3/2010 | Hoffmann | |
| 2010/0068170 A1 | 3/2010 | Michal et al. | |
| 2010/0137975 A1 | 6/2010 | Wittchow | |
| 2010/0198190 A1* | 8/2010 | Michal ............... | A61K 31/337 604/509 |
| 2010/0233236 A1 | 9/2010 | Zhao | |
| 2010/0278744 A1 | 11/2010 | Speck et al. | |
| 2010/0278997 A1 | 11/2010 | Speck et al. | |
| 2011/0015664 A1 | 1/2011 | Kangas et al. | |
| 2011/0015725 A1 | 1/2011 | Bates et al. | |
| 2011/0070355 A1 | 3/2011 | Bavaro et al. | |
| 2011/0143014 A1 | 6/2011 | Stankus et al. | |
| 2011/0144577 A1 | 6/2011 | Stankus et al. | |
| 2011/0196340 A1 | 8/2011 | Barry et al. | |
| 2011/0295200 A1 | 12/2011 | Speck et al. | |
| 2012/0015019 A1* | 1/2012 | Pacetti ............... | A61K 31/337 424/422 |
| 2012/0064141 A1 | 3/2012 | Andreacchi et al. | |
| 2012/0064223 A1 | 3/2012 | Gamez et al. | |
| 2012/0076920 A1 | 3/2012 | Michal et al. | |
| 2012/0078227 A1* | 3/2012 | Kangas ............... | A61L 29/043 604/509 |
| 2012/0078228 A1 | 3/2012 | Michal et al. | |
| 2012/0135133 A1 | 5/2012 | O'Neill et al. | |
| 2012/0165922 A1 | 6/2012 | Gong et al. | |
| 2012/0239001 A1 | 9/2012 | Barry et al. | |
| 2012/0289933 A1 | 11/2012 | Michal et al. | |
| 2013/0053947 A1 | 2/2013 | Kangas et al. | |
| 2013/0129814 A1 | 5/2013 | Pacetti et al. | |
| 2013/0189329 A1 | 7/2013 | Wang | |
| 2013/0197436 A1 | 8/2013 | Wang | |
| 2013/0231638 A1 | 9/2013 | Speck et al. | |

FOREIGN PATENT DOCUMENTS

| | | |
|---|---|---|
| EP | 1011171 A2 | 6/2000 |
| EP | 1118325 A2 | 7/2001 |
| EP | 1632259 A2 | 3/2006 |
| EP | 1649853 A2 | 4/2006 |
| WO | 91/12779 A1 | 9/1991 |
| WO | 93/11120 A1 | 6/1993 |
| WO | 94/16706 A1 | 8/1994 |
| WO | 95/03036 A1 | 2/1995 |
| WO | 98/58988 A1 | 12/1998 |
| WO | 99/08729 A1 | 2/1999 |
| WO | 01/28589 A2 | 4/2001 |
| WO | 02/076509 A2 | 10/2002 |
| WO | 2004/028582 A1 | 4/2004 |
| WO | 2004/028610 A2 | 4/2004 |
| WO | 2005044506 A1 | 5/2005 |
| WO | 2006/022754 A2 | 3/2006 |
| WO | 2007/035865 A1 | 3/2007 |
| WO | 2007/094940 A2 | 8/2007 |
| WO | 2007/111885 A2 | 10/2007 |
| WO | 2007/112006 A2 | 10/2007 |
| WO | 2007143159 A2 | 12/2007 |
| WO | 2008003298 A2 | 1/2008 |
| WO | 2008/031596 A1 | 3/2008 |
| WO | 2008/104573 A2 | 9/2008 |
| WO | 2009/036014 A2 | 3/2009 |
| WO | 2009/124570 A1 | 10/2009 |
| WO | 2010/030995 A2 | 3/2010 |
| WO | 2011106027 A1 | 9/2011 |

OTHER PUBLICATIONS

Official Action issued in Japanese Application No. 2012-554976 dated Jan. 8, 2015.

International Search Report and Written Opinion dated Apr. 14, 2015 from Int'l Appl. No. PCT/US2015/010786.

Notification of Reexamination from Chinese Appl. No. 201080064497.3 dated Jul. 8, 2015.

International Preliminary Report on Patentability and Written Opinion of the International Searching Authority from Appl. No. PCT/US2015/010786 dated Aug. 4, 2016.

Official Action issued in Japanese Application No. 2012-554976 dated Apr. 2, 2014.

Katsuda, S., et al., "The Role of Cytoplasmic Microtubules in Regulation of Smooth Muscle Proliferation", 8th International Symposium on Atherosclerosis, p. 446, (1988).

Gray, W.A., et al., "Drug-Coated Balloons for the Prevention of Vascular Restenosis", Circulation, pp. 2672-2680 (2010).

Weaver, J.V.M., et al., "Stimulus-Responsive Water-Soluble Polymers Based on 2-Hydroxyethyl Methacrylate", Macromolecules, vol. 37, pp. 2395-2403 (2004).

Jones, D.S., et al., "Poly(e-caprolactone) and poly(e-caprolactone)-polyvinylpyrrolidone-iodine blends as ureteral biomaterials: characterisation of mechanical and surface properties, degradation and resistance of encrustation in vitro", Biomaterials, vol. 23, pp. 4449-4458 (2002).

Consigny, P.M., PhD., et al., "Local Delivery of an Antiproliferative Drug with Use of Hydrogel-coated Angioplasty Balloons!", Journal of Vascular and Interventional Radiology, vol. 5, No. 4, pp. 553-560 (1994).

Y. Fu, et al., "Medicinal Chemistry of Paclitaxel and its Analogues", Current Medicinal Chemistry, vol. 16, pp. 1-20 (2009).

Steven J. Sollott, et al., "Taxol Inhibits Neointimal Smooth Muscle Cell Accumulation after Angioplasty in the Rat", The Journal of Clinical Investigation, Inc., vol. 95, pp. 1869-1876 (1995).

B. Braun Vascular Systems, "SeQuent® Please", Product Brochure No. 6050120, accessed Sep. 9, 2009 at <http://www.deb-bbraun.com/doc/doc> download.cfm?6736&uuid=9E5F74B02A5AE6266471CF5AF5F43933&&IRACER_AUTOLINK &&, B. Braun Melsungen AG Vascular Systems, 10 pages, Berlin, Germany.

First Examination Report dated Apr. 22, 2015 from New Zealand Appl. No. 701765.

Australian Examination Report issued in Appl. No. AU 2015209714 dated Nov. 16, 2017.

* cited by examiner paclitaxel Tissue Uptake (μg) - Single Deployment (n=5)

Residual paclitaxel (%) on Balloon - Single Deployment (n=5)

*Error bar = ± 1 standard deviation paclitaxel Tissue Uptake (μg) – Single vs. Multiple Deployments (n=2)

*Error bar = ± 1 standard deviation

Residual paclitaxel (%) on Balloon – Single vs. Multiple Deployments (n=2)

3B Humidified vs. non-Humidified Balloon Elution Profile

COATINGS FOR MEDICAL DEVICES

FIELD

The present disclosure provides coatings for medical devices and the delivery of therapeutic agents therefrom. In embodiments, the present disclosure relates to methods and devices used for local delivery of water-soluble or water-insoluble therapeutic agents to the surface of normal or diseased body lumens.

BACKGROUND

Sporadic, inherited, environmental, and iatrogenic diseases associated with significant morbidity and mortality may develop in the wall of endothelial cell-lined and epithelial cell-lined body lumens. For example, atherosclerosis and post-procedural restenosis develop in the arterial wall. Adenocarcinoma, esophageal varices, and cholangiocarcinoma develop in the gastrointestinal tract wall.

The efficacy of systemic drug therapy for these diseases may be limited by inadequate drug delivery to the diseased tissue and/or dose limiting toxic effects in non-diseased tissue. Local delivery of drugs to diseased tissue in body lumen walls can be difficult.

SUMMARY

The present disclosure provides medical devices and methods for treating body lumens with the devices. In embodiments, the medical devices include a catheter assembly for insertion into the vasculature. The catheter assembly includes an expandable structure having an outer surface, a non-durable coating including a polymer matrix disposed on the outer surface of the expandable structure, and a therapeutic agent dispersed throughout the polymer matrix, wherein the coating has a therapeutic agent density of from about 0.1 $\mu g/mm^2$ to about 1.5 $\mu g/mm^2$.

In other embodiments, a catheter assembly of the present disclosure, for insertion into the vasculature, includes an expandable structure having an outer surface, a non-durable coating including a polymer matrix complexed with iodine disposed on the outer surface of the expandable structure, and a therapeutic agent dispersed in the matrix complexed with the iodine, wherein the coating has a therapeutic agent density of from about 0.1 $\mu g/mm^2$ to about 1.5 $\mu g/mm^2$.

In yet other embodiments, a catheter assembly of the present disclosure, for insertion into the vasculature, includes an expandable structure having an outer surface, a non-durable coating including a polymer matrix of polyethylene glycol disposed on the outer surface of the expandable structure, and a therapeutic agent including paclitaxel dispersed throughout the polymer matrix, wherein the coating has a therapeutic agent density of from about 0.1 $\mu g/mm^2$ to about 1.5 $\mu g/mm^2$, and wherein the coating has a thickness from about 0.01 $\mu m$ to about 10 $\mu m$.

As noted above, methods of using these devices are also provided. In embodiments, the methods include introducing a catheter assembly of the present disclosure into a patient's vasculature, and expanding the expandable structure in the vasculature for a period from about 5 seconds to about 300 seconds so the polymer coating contacts a wall of a body lumen and transfers the therapeutic agent to the wall of the body lumen.

DETAILED DESCRIPTION

Figure 1A:
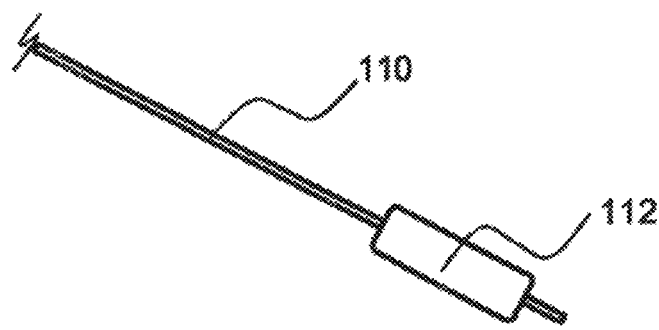
FIG. 1A is a side view illustration of a balloon catheter while the balloon is in the expanded position.

Embodiments of the present disclosure include methods and devices used for local delivery of water-soluble or water-insoluble therapeutic agents to the surface of normal or diseased body lumens. Therapeutic concentrations of drugs can be delivered without systemic toxicity. Surprisingly, it has been found that coatings of the present disclosure, while thinner than conventional coatings possessing comparable materials, are very efficient in drug delivery. Coatings of the present disclosure, while possessing lower dosages of drug therein when compared with commercially available conventional coatings, are capable of delivering comparable amounts of drug(s) in vivo. Thus, much lower doses of drugs than those conventionally used in coatings can be used to still achieve bio-equivalence.

In addition, coatings of the present disclosure, even after multiple deployments, can deliver comparable amounts of drug(s) when compared with a first deployment of a balloon possessing a conventional coating, thus permitting re-use of a balloon at multiple sites in vivo, without the need to introduce a new balloon into a patient.

Various embodiments described herein are described with reference to figures. However, certain embodiments may be practiced without one or more of these specific details, or in combination with other known methods and configurations. In the following description, numerous specific details are set forth, such as specific configurations, compositions, and processes, etc., in order to provide a thorough understanding of the present disclosure. In other instances, well-known processes and manufacturing techniques have not been described in particular detail in order to avoid obscuring the present disclosure.

Any medical device may be coated in accordance with the present disclosure. Medical devices of the present disclosure include, but are not limited to, stents, catheters, balloons, bronchoscopes, dilators, combinations thereof, and the like. Embodiments of the disclosure include a medical disposable device in which an amphiphilic polymer coating is disposed on the outer surface of an expandable structure. In embodiments, the medical disposable device is a catheter with an expandable balloon having a polymer coating including a therapeutic agent dispersed in the coating. The polymer coating, in embodiments, may include at least one therapeutic agent and at least one amphiphilic polymer or co-polymer. The polymer coating may optionally include additional components such as plasticizers and/or waxes. The therapeutic agent can be either water-soluble or water-insoluble.

Amphiphilic Polymers or Co-polymers

In embodiments, a polymer coating of the present disclosure includes one or more amphiphilic polymers or co-polymers. Suitable amphiphilic polymers or co-polymers include non-ionic thermoplastic polymers or co-polymers. For example, the amphiphilic polymer may be hydroxypropyl cellulose (HPC), polyvinyl pyrrolidone (PVP), polyethylene glycol (PEG), methyl cellulose, hydroxypropyl methylcellulose, or co-polymers of N-vinylpyrrolidone with other reactive, double-bond containing monomers such as styrene, acrylic acid, vinyl acetate, vinyl caprolactam, combinations thereof, and the like.

The amphiphilic polymer may also be a poly(hydroxyethyl methacrylic) acid, also known as poly(HEMA). In embodiments, the poly(HEMA) has a number average molecular weight, Mn, below approximately 8 KD. In other embodiments, the poly(HEMA) has a number average molecular weight, Mn, of approximately 7 KD. The amphiphilic polymer may also be a co-polymer of HEMA with a monomer such as, but not limited to, glycidyl methacrylate (GMA) or acrylic acid. Co-polymers can be block or random. Methods for producing suitable poly(HEMA) include those disclosed in U.S. Patent Application Publication No. 2012/0076920, the entire disclosure of which is incorporated by reference herein.

In other embodiments, polyethylene glycol (PEG) may be used as the amphiphilic polymer. In embodiments, the PEG has a molecular weight from about 1.5 KD to about 50 KD.

In embodiments, the amphiphilic polymer or co-polymer is optionally complexed with iodine and the iodine is not covalently bonded to the amphiphilic polymer or co-polymer. For example, PVP, PEG, HPC and poly(HEMA) may be complexed with iodine. PVP complexed with iodine is also known as povidone iodine.

Where the amphiphilic polymer is complexed with iodine, the weight of the polymer-iodine complex may vary. For example, poly(HEMA) complexed with iodine has a number average molecular weight, Mn, below approximately 8 KD, for example 7 KD. PEG complexed with iodine has as molecular weight of 1.5 KD to 50 KD.

Where the amphiphilic polymer is complexed with iodine, the iodine can serve certain functions. For example, iodine imparts an amber hue to the polymer coating, aiding in visualization outside of the body, and with the coating process. Additionally, as iodine has a large nuclear radius, it can provide radiopacity under fluoroscopy; medical devices possessing coatings of the present disclosure may be visible under fluoroscopy, and the dissolution of the polymer coating can be monitored as a function of time.

In other embodiments, the amphiphilic polymer or co-polymer is an ionic thermoplastic co-polymer or co-polymer. For example, the amphiphilic polymer or co-polymer can be poly (methyl vinyl ether-alt-maleic acid monobutyl ester) (available under the trade name GANTREZ ES-425, from International Specialty Products (ISP), Wayne, N.J.) or poly (methyl vinyl ether-alt-maleic acid monoethyl ester) (available under the trade name GANTREZ ES-225, from International Specialty Products (ISP), Wayne, N.J.).

In embodiments, the polymer coating may optionally include a plasticizer in the polymer matrix. A plasticizer may be useful to increase the ductility and prevent the coating from cracking or delaminating while bending or folding in the dry state. Suitable plasticizers include, but are not limited to, propylene glycol, triethyl citrate, glycerol, and dibutyl sebacate. In embodiments, the plasticizer is present at 30% to 85% by weight of the amphiphilic polymer.

In embodiments, the polymer coating may optionally include a wax in the polymer matrix. A wax-like surface assists with the gliding quality of the amphiphilic polymer coating in relation with a body lumen surface and/or in relation with an optional protective sheath over the amphiphilic polymer coating. Suitable waxes include, but are not limited to, bees wax, carnauba wax, polypropylene glycol, polydimethyl siloxane (PDMS), and PDMS derivatives.

Hydration of the polymer coating occurs upon exposure to aqueous fluids, such as blood in vivo, which may enhance release of the therapeutic agent into tissue of the body lumen.

Without wishing to be bound by any theory, it is believed the expansion of the expandable structure physically embeds the therapeutic agent in the wall defining a lumen to which the expandable structure comes in contact.

Solvents/Other Components

The term amphiphilic as used herein means polymers used to form coatings of the present disclosure are at least partially dissolvable in water, as well as aqueous solutions such as, but not limited to, blood, as well as at least partially dissolvable in non-aqueous solutions possessing solvents such as, but not limited to, ethanol, methanol, and/or isopropanol. Accordingly, an "amphiphilic polymer coating" and "amphiphilic polymer or co-polymer" according to embodiments of the disclosure are at least partially dissolvable in aqueous solvents or solutions, non-aqueous solvents or solutions, or both.

In some embodiments, the amphiphilic polymer or co-polymer is fully amphiphilic, meaning fully dissolvable in both aqueous and non-aqueous solvents.

In other embodiments, the amphiphilic polymer or co-polymer is not fully amphiphilic. For example, the amphiphilic polymer or co-polymer may exhibit significant or total solubility in aqueous solvents, but the amphiphilic polymer or co-polymer may exhibit only partial solubility in non-aqueous solvents.

In some embodiments, water may be added to a coating solution in order to dissolve the amphiphilic polymer or co-polymer. For example, a coating solution may be prepared in which the amphiphilic polymer or co-polymer and a water-insoluble therapeutic agent are dissolved in a mixture of aqueous and non-aqueous solvents. In embodiments, the coating solution contains a majority of non-aqueous solvents. In embodiments, the coating solution contains a ratio from about 100% to about 80% non-aqueous solvent, and from about 0% to about 20% aqueous solvent.

In other embodiments, additional components may be included in the amphiphilic polymer coating. These additional components may not necessarily be dissolvable in both aqueous and non-aqueous solvents, yet the aggregate polymer matrix of the amphiphilic polymer coating is at least partially dissolvable in both aqueous and non-aqueous solvents utilized in the coating solution. For example, embodiments of the disclosure may utilize water-soluble and/or water-insoluble therapeutic agents, as well as water-insoluble waxes or other components inter-dispersed in the aggregate polymer matrix of the amphiphilic polymer coating.

In embodiments, a minority weight percent of a hydrophobic polymer or co-polymer can be included in the polymer matrix of the amphiphilic polymer coating. For example, a small minority of hydrophobic polymer or co-polymer could be added to extend the lifetime of the coating in vivo, or slightly retard the release rate of the therapeutic agent, while still allowing rapid and uniform dissolution of the coating in vivo.

In embodiments, an amphiphilic polymer coating may include a substantially water-insoluble component dispersed within an amphiphilic polymer or co-polymer.

Therapeutic Agents

Embodiments of the present disclosure include an apparatus and method for delivering therapeutic agents to treat a variety of diseases that arise in body lumen walls. The therapeutic agents useful in accordance with the present disclosure may be used singly or in combination. The therapeutic agents may be non-aqueous soluble (i.e. solvent soluble) and/or aqueous soluble. In embodiments, the dried coating has a therapeutic agent (drug) to polymer matrix weight ratio (D/P) from 25-100%. As used herein the D in the D/P ratio includes all of the drugs in the coating unless the D/P ratio is utilized differently to specifically represent a single drug in the coating. As used herein the P in the D/P ratio includes all of the amphiphilic polymer and/or co-polymer(s), and additional components such as plasticizer and wax dispersed or otherwise uniformly integrated into the polymer matrix. The D/P may depend upon the molecular weight of the amphiphilic polymer and/or co-polymer, and the presence of additional components such as a plasticizer and/or wax.

In embodiments, the dried coating has a therapeutic agent (drug) density of from about 0.1 $\mu g/mm^2$ to about 1.5 $\mu g/mm^2$ when the balloon is inflated to Nominal Inflation Pressure, in embodiments from about 0.25 $\mu g/mm^2$ to about 0.8 $\mu g/mm^2$ when the balloon is inflated to Nominal Inflation Pressure, in other embodiments from about 0.4 $\mu g/mm^2$ to about 0.6 $\mu g/mm^2$ when the balloon is inflated to Nominal Inflation Pressure. The drug density may vary depending upon factors such as the specific drug and polymer matrix selections. In embodiments, the dried coating is present on a catheter balloon, the drug is paclitaxel (sometimes abbreviated, herein, as PTX), and the amphiphilic polymer is PEG, and the dried coating has a paclitaxel density of approximately 0.1-1.5 $\mu g/mm^2$ when the balloon is inflated to Nominal Inflation Pressure.

Compared with a balloon possessing a coating with similar polymers and/or excipients and therapeutic agents, the drug density of a coating of the present disclosure is much lower, as current balloons have a drug density from about 2 to about 4 $\mu g/mm^2$.

In embodiments, non-aqueous soluble and/or water-insoluble therapeutic agents are particularly useful as components in a coating composition which includes a majority of non-aqueous solvents. For example, a non-aqueous soluble anti-proliferative agent such as paclitaxel may be used in combination with another therapeutic agent such as the anti-inflammatory agent dexamethasone. In embodiments, therapeutic agents which may be, singly or in combination, locally delivered to the surface of normal or diseased body lumens can be classified into the categories of anti-proliferative agents, anti-platelet agents, anti-inflammatory agents, anti-thrombotic agents, and thrombolytic agents.

Classes of therapeutic agents can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of non-aqueous soluble vinca alkaloids include, but are not limited to, paclitaxel (including the alkaloid itself and naturally occurring forms and derivatives thereof, as well as synthetic and semi-synthetic forms thereof), vincristine, etoposide, indirubin, and anthracycline derivatives, such as, for example, daunorubicin, daunomycin, and plicamycin. Other sub-classes of anti-mitotic agents include anti-mitotic alkylating agents, such as, for example non-aqueous soluble fotemustine, and anti-mitotic metabolites, such as, for example, non-aqueous soluble azathioprine, mycophenolic acid, leflunomide, teriflunomide, fluorouracil, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Examples of non-aqueous soluble anti-inflammatory agents that can also be used include, but are not limited to, dexamethasone, prednisone, hydrocortisone, estradiol, triamcinolone, mometasone, fluticasone, clobetasol, and non-steroidal anti-inflammatories, such as, for example, acetaminophen, ibuprofen, and sulindac. The arachidonate metabolite prostacyclin or prostacyclin analogs are examples of a vasoactive antiproliferative.

Therapeutic agents with pleiotropic effects on cell proliferation, immunomodulation and inflammation may also be used. Examples of such non-aqueous soluble agents include, but are not limited to the macrolides and derivatives thereof such as sirolimus (e.g. rapamycin), tacrolimus, everolimus, temsirolimus and umirolimus (biolimus A9)

Anti-platelet agents are therapeutic entities that act by (1) inhibiting adhesion of platelets to a surface, such as a thrombogenic surface, (2) inhibiting aggregation of platelets, (3) inhibiting activation of platelets, or (4) combinations of the foregoing. Non-aqueous soluble anti-platelet agents that act as inhibitors of adhesion of platelets include, but are not limited to tirofiban and RGD, (Arg-Gly-Asp)-based peptides (Pegylated) that inhibit binding to gpIIbIIIa or αvβ3, and/or compounds that block P-selectin or E-selectin binding to their respective ligands. Agents that inhibit ADP-mediated platelet aggregation include, but are not limited to, cilostazol.

Anti-thrombotic agents include chemical and biological entities that can intervene at any stage in the coagulation pathway. Examples of specific non-aqueous soluble entities include, but are not limited to, small molecules that inhibit the activity of factor Xa. Also included are direct thrombin inhibitors, such as, for example, argatroban, inogatran.

Other non-aqueous soluble therapeutic agents that can be used include cytotoxic drugs, such as, for example, apoptosis inducers and topoisomerase inhibitors, including, irinotecan and doxorubicin, and drugs that modulate cell differentiation such as inhibitors of histone deacetylase, including valproic acid.

Other non-aqueous soluble therapeutic agents that can be used include anti-lipidemic agents, including but not limited to fenofibrate, clofibrate, and rosiglitazone and matrix metalloproteinase inhibitors, such as, for example, batimistat, antagonists of the endothelin-A receptor, such as, for example, darusentan.

In other embodiments, aqueous soluble therapeutic agents may be used. Aqueous soluble anti-mitotic agents include Epothilone A, Epothilone B and Epothilone D, and all other Epothilones. Aqueous soluble anti-platelet agents include RGD (Arg-Gly-Asp)-based peptides that inhibit binding to gpIIbIIIa or αvβ3. Aqueous soluble anti-thrombotic agents include heparinoid-type agents that can inhibit both FXa and thrombin, either directly or indirectly, such as, for example, heparin, heparin sulfate, low molecular weight heparins, such as, for example, the compound sold as CLIVARIN®, and synthetic oligosaccharides, such as, for example, the compound sold as ARIXTRA®. Aqueous soluble thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase. Additional aqueous soluble therapeutic agents include recombinant antibodies for anti-platelet and anti-endothelin applications.

When used in any treatment, a therapeutically effective amount of one of the non-aqueous soluble or aqueous soluble therapeutic agents may be employed in pure form or, where such forms exist, in pharmaceutically acceptable salts, esters or prodrug forms.

Alternatively, the therapeutic agent may be administered as a pharmaceutical composition including the compound of interest in combination with one or more pharmaceutically acceptable excipients. As used herein, the phrase "therapeutically effective amount" of the therapeutic agents of the disclosure means a sufficient amount of the therapeutic agents to treat disorders, at a reasonable benefit/risk ratio applicable to any medical treatment. It will be understood, however, that the total daily usage of the therapeutic agents and compositions of embodiments of the disclosure will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the therapeutic agent at levels lower than required to achieve the desired therapeutic effect, and to gradually increase the dosage until the desired effect is achieved.

In embodiments, a coating of the present disclosure may include amphiphilic polymer, therapeutic agent, and optionally iodine. The polymer may be present in an amount from about 5% to about 75% by weight of the coating, in embodiments from about 15% to about 60% by weight of the coating, in other embodiments from about 25% to 50% by weight of the coating. The therapeutic agent may be present in an amount from about 25% to about 95% by weight of the coating, in embodiments from about 35% to about 85% by weight of the coating, in embodiments from about 45% to about 75% by weight of the coating. The iodine may be present in an amount from about 0% to about 5% by weight of the coating, in embodiments from about 1% to about 4% by weight of the coating, in embodiments from about 2% to about 3.5% by weight of the coating.

In embodiments, a coating of the present disclosure may be suitable for application in touch and go procedures where the therapeutic agent transfer takes place within, for example, from about 5 seconds to about 300 seconds, in embodiments from about 30 seconds to about 240 seconds after inflation.

Coating Process

Figure 1B:
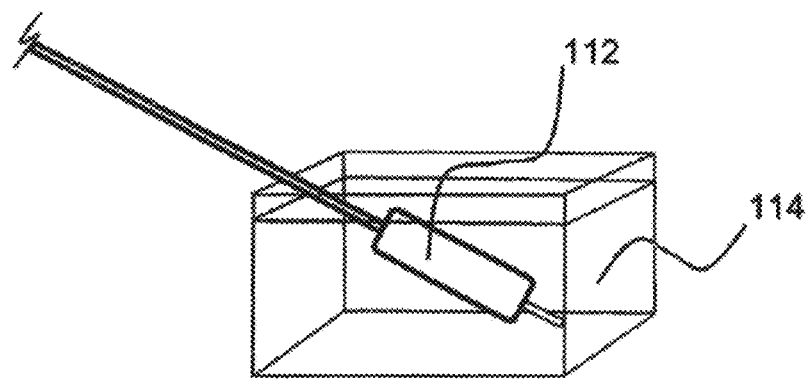
FIG. 1B is an isometric view illustration of a balloon catheter dipped in a coating solution while the balloon is in the expanded position.
Figure 1C:
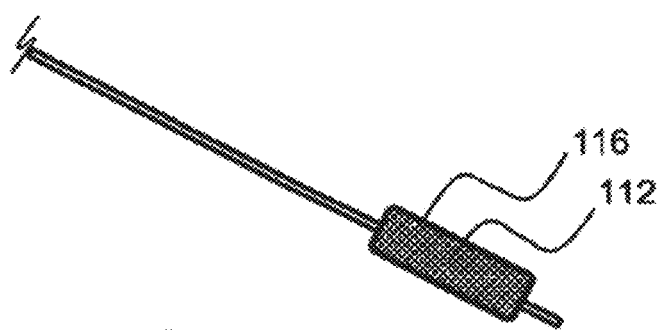
FIG. 1C is a side view illustration of a balloon catheter with a coated balloon surface.

The amphiphilic polymer coating containing a therapeutic agent or agents and an amphiphilic polymer or co-polymer can be formed from with a variety of techniques including deposition, spray coating, and dip coating. FIG. 1A-FIG. 1C are illustrations of embodiments in which the amphiphilic polymer coating is formed by dip coating the expandable structure of a medical disposable device, such as the balloon of a balloon catheter, into a coating solution or coating mixture. Utilizing embodiments of the disclosure, the dip coating process can provide a uniform therapeutic agent density across the balloon surface using a simple and reproducible single-dip, thereby eliminating the need for multiple dips to load the therapeutic agent into the coating.

FIG. 1A is an illustration of a balloon catheter 110 with an uncoated balloon 112 in the expanded position (e.g. inflated). As shown in FIG. 1B, the uncoated expanded balloon 112 can be dipped into a coating solution or mixture 114 and then extracted from coating solution 114. As described above, the coating solution 114 may include mixtures of aqueous or non-aqueous solvents, an amphiphilic polymer or co-polymer, and a therapeutic agent. The coating solution 114 may optionally include additional components such as a plasticizer and/or wax.

In embodiments, the coating solution 114 viscosity is at least 5 cps and less than approximately 75 cps. After dipping the expanded balloon 112 into the coating solution 114, the expanded balloon 112 is then removed from the coating solution, as shown in FIG. 1C, resulting in a uniform coating 116 on the expanded balloon 112. In embodiments, optionally a gas (e.g. argon, oxygen) plasma may be used on the catheter prior to coating to enhance coating adhesion.

In embodiments, the use of an amphiphilic polymer or co-polymer and non-aqueous soluble therapeutic agent enables the use of non-aqueous solvents to dissolve the polymer or co-polymer and therapeutic agent. In alternate embodiments, where the therapeutic agent and/or amphiphilic polymer or co-polymer is not fully soluble in non-aqueous solutions, an aqueous solution or a solution including a mixture of aqueous and non-aqueous solvents may be used.

A majority or exclusively non-aqueous solvents in the coating solution provide rapid evaporation, a lower surface tension, and improved substrate wetting compared to an aqueous solution, which aids in obtaining coating uniformity. In embodiments, a suitable coating solution may contain a ratio in the range of 100% to 80% non-aqueous solvent, and 0% to 20% aqueous solvent. For example, solvents with boiling points lower than water can be used singly or in combination in the coating solution 114, such as ethanol, methanol, or methyl ethyl ketone, acetonitrile, isopropanol (2-propanol), and/or butanol that rapidly evaporate in ambient conditions, which consequently reduces gravity induced surface defects such as sagging.

The coating solution 114 may be prepared by mixing the therapeutic agent, solvent(s), polymer(s) and other components such as plasticizer into a single container. Several mixing and/or dissolving operations may be also performed prior to combining multiple solutions to form the coating solution 114. For example, where an amphiphilic polymer or co-polymer is complexed with iodine, a complexed polymer solution may be prepared. For example, $I_2$ may be dissolved in alcohol (or a solution having a ratio of up to 80/20 non-aqueous and aqueous solvents), then dry polymer powder is added to the $I_2$ and alcohol. Agitation and/or heat may be applied to the solution to dissolve the polymer. For example, 0.05 grams of $I_2$ is dissolved in 12 grams of 2-propanol. Then 1.00 grams of PVP (360 KD, ISP) is added. The suspension is shaken continuously until the PVP is dissolved, about 1 hour. In an embodiment, the resulting solution is a 20% povidone-iodine in 2-propanol solution.

The therapeutic agent can then be dissolved in a separate alcohol, alcohol and acetone solution, or a solution having a ratio of up to 80/20 non-aqueous and aqueous solvents. For example, 0.1 grams paclitaxel is dissolved in 0.1 grams ethanol and 0.18 grams of 50% PEG-400 in acetone at 40° C. This solution can then be cooled to room temperature and added to 0.55 grams of the 20% povidone-iodine in 2-propanol solution. In an embodiment, the combined coating solution has a drug (i.e. paclitaxel) to polymer matrix (i.e. iodinated-PVP and PEG-400) ratio (D/P) of 50%, the solution is 31.8% non-volatile, and the drug (i.e. paclitaxel) is 33% of the non-volatile. After coating, the balloon is dried, deflated and folded for delivery. In an embodiment, after the balloon is dried, but before deflating and folding for delivery, the balloon may optionally be dip coated into a separate coating solution containing a wax to form a thin wax coating (not shown) over the amphiphilic polymer coating, rather than incorporating the wax into the amphiphilic polymer coating.

Once applied to a medical device, in embodiments a balloon of a balloon catheter, coatings of the present disclosure may have a thickness from about 0.01 μm to about 10 μm, in embodiments from about 0.05 μm to about 5 μm, in embodiments from about 0.1 μm to about 2 μm. This may be much thinner than conventional balloon coatings including polymers and/or similar excipients and therapeutic agents, which may have a thickness of from about 5 μm to about 30 μm. Thinner coatings may be advantageous as they will have a smaller profile, and thus may be more maneuverable in vivo, including where used in the vasculature.

In addition, the thinner coatings achieved in accordance with the present disclosure have better coating integrity and are less likely to undergo flaking, delamination, etc. This is due to the fact, at least in part, that the thin coating acts less like a singular film, and more like individual, smaller pieces, which are less likely to fragment when exposed to stresses including expansion and contraction. As the coating thus maintains its integrity, more of the coating, and therefore more of the drug in such a coating, can reach the treatment site.

Local Therapeutic Agent Delivery Process

Figure 2A:
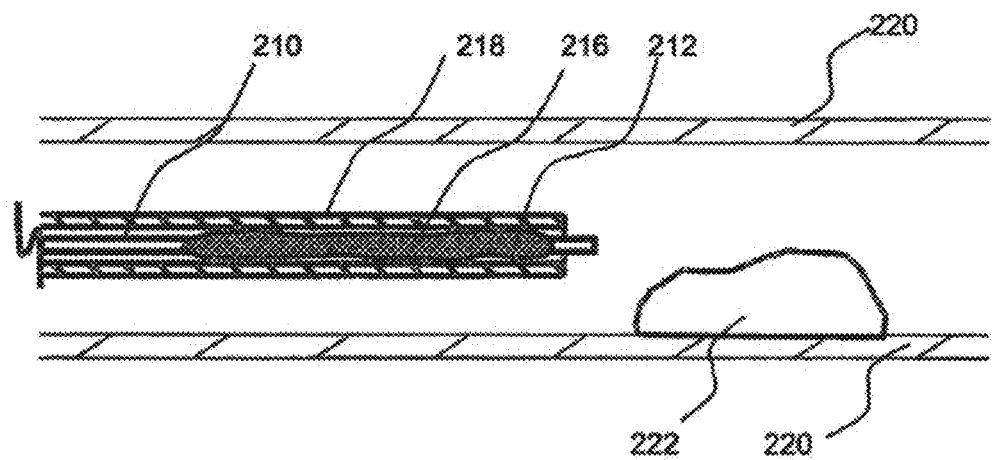
FIG. 2A is a side view illustration of a polymer coating disposed on an outer surface of unexpanded balloon of a balloon catheter covered by a retractable sheath and inserted into a body lumen.
Figure 2B:
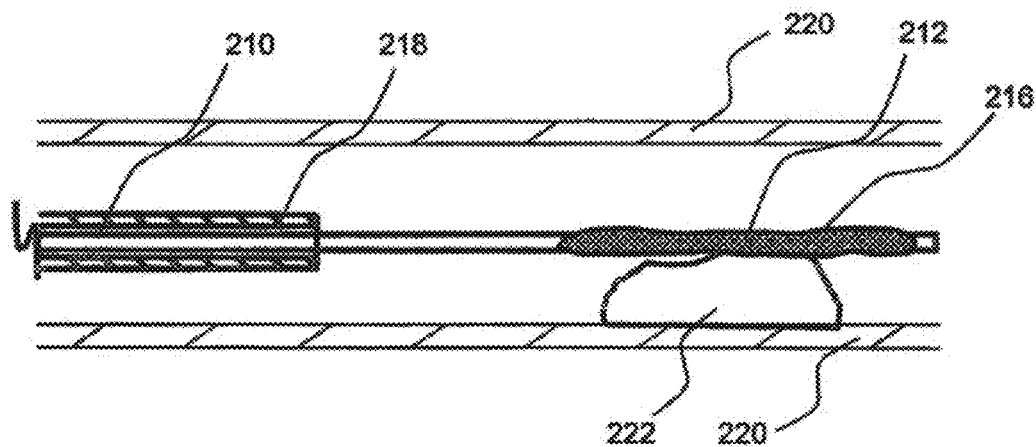
FIG. 2B is a side view illustration of a polymer coating disposed on an outer surface of unexpanded balloon of a balloon catheter adjacent to the focal area of local therapeutic agent delivery within a body lumen.
Figure 2C:
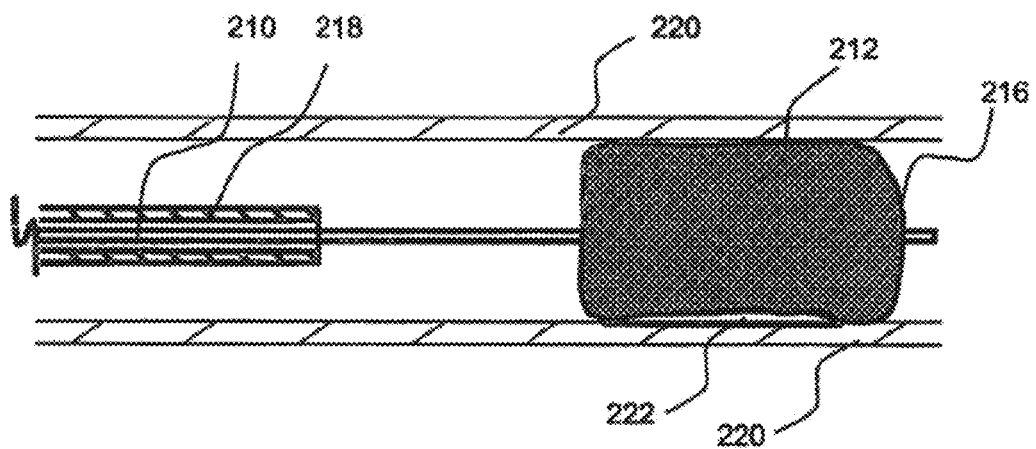
FIG. 2C is a side view illustration of the interface of the polymer coating disposed on an outer surface of an expanded balloon of a balloon catheter and the focal area of local therapeutic agent delivery within a body lumen.

FIG. 2A-FIG. 2C are illustrations of embodiments in which the amphiphilic polymer coating possessing a therapeutic agent and amphiphilic polymer or co-polymer is locally delivered to the surface of a body lumen. As shown in FIG. 2A, a balloon catheter 210 having an amphiphilic polymer coating 216 disposed on an unexpanded balloon 212 is provided and inserted into a body lumen defined by wall 220. The catheter 210 may additionally include an optional protective sheath 218 over the unexpanded balloon 212 to prevent the amphiphilic polymer coating 216 from prematurely dissolving when the catheter is inserted into the body lumen defined by wall 220. In embodiments, the body lumen may be an artery having wall 220 including a focal area 222, such as an unperturbed primary atherosclerotic or restenotic lesion. In other embodiments, the wall 220 defining the body lumen may be a common bile duct or a branch of a common bile duct and focal area 222 is an intraluminal tumor.

As shown in FIG. 2B, the unexpanded balloon 212 is positioned adjacent the focal area 222 and the protective sheath 218 is retracted. The balloon 212 is then expanded (by inflation or otherwise) to contact the amphiphilic polymer coating 216 on the expanded balloon 212 against the wall 220 of the body lumen where the focal area 222 exists. In embodiments, the expanded balloon 212 is a balloon catheter and the balloon is expanded to 2-20 atmospheres. In embodiments, expansion of balloon 212 so that it contacts wall 220 defining a body lumen where focal area 222 exists permits transfer of therapeutic agent (not shown) from balloon 212 to focal area 222. This transfer of therapeutic agent may be referred to, in embodiments, as a "touch and go" procedure.

Surprisingly, it has been found that coatings of the present disclosure, although thinner than conventional coatings, may be able to deliver the same amount of therapeutic agent when compared to conventional coatings. Moreover and also surprisingly, coatings of the present disclosure may be able to deliver the same or comparable amounts of therapeutic agents when compared to conventional coatings, even after multiple uses/deployments.

In clinical use for angioplasty, it may be desirable for the balloon 212 to be expanded for only 5 to 300 seconds, in embodiments from about 30 to about 90 seconds, in a touch and go procedure. This time limitation is due to the type of medical procedure, as a longer use time with the balloon inflated could result in focal or adjacent tissue damage that is deleterious to the therapeutic intent of the procedure. This damage could result from mechanical pressure and/or metabolic insufficiency caused by sustained inflation of the balloon.

In embodiments, a coated angioplasty balloon may be tracked to a target lesion using standard techniques, the optional protective sheath is retracted, and the angioplasty balloon is inflated against an artery wall. Hydration of the coating may assist in releasing the therapeutic agent into tissue.

In use, the catheter may be advanced within a body lumen to align the balloon with the target tissue, the balloon is expanded to 2-20 atmospheres to bring the amphiphilic polymer coating into contact with the target tissue, causing the therapeutic agent payload to release rapidly to the target tissue in vivo. The device only contacts the target tissue for a short amount of time, from about 5 to about 300 seconds. Because the device is to be used for only a short time period and then removed from the body, it is considered to be a "medical disposable" device rather than "implantable" device.

In accordance with the present disclosure, a significant portion of the therapeutic agent contained in the coating may be transferred to the tissue of the surrounding lumen during the procedure. In embodiments, from about 1% to about 25% of the therapeutic agent contained in the coating is imparted into the tissue of a vascular lumen upon inflation of the balloon, in embodiments, from about 5% to about 15% of the therapeutic agent contained in the coating is imparted into the tissue of a vascular lumen upon inflation of the balloon, in other embodiments from about 7% to about 12% of the therapeutic agent contained in the coating is imparted into the tissue of a vascular lumen upon inflation of the balloon.

Medical devices of the present disclosure may be used to treat a variety of diseases. Exemplary maladies/diseases which may be treated with devices of the present disclosure are set forth below.

Diseases of the Vasculature

One therapeutic area where embodiments of the present disclosure may be applicable is the treatment of luminal disorders of the vasculature. In general, luminal disorders may be classified as native (atherosclerotic, thromboembolic) or iatrogenic (restenosis) diseases. These luminal disorders may include, but are not limited to, atherosclerosis, atheromatous lesions, vulnerable plaque, thromboembolic obstructions, vascular graft disease, arteriovenous fistula disease, arteriovenous graft disease and restenosis.

Specifically, embodiments of the present disclosure could be applied to a catheter with a tip that is expandable to allow uniform and complete contact with and delivery of therapeutic agents to sites of luminal atheromatous or vulnerable plaques. The local delivery of therapeutic agents would enable a much higher, targeted, local concentration of said agents than might otherwise be achieved by systemic delivery. Moreover, a local delivery strategy would enable the use of therapeutic agents that otherwise may be poor candidates for systemic delivery due to lack of bioavailability and/or undesirable or toxic side effects at concentrations needed to achieve efficacy.

Restenosis

Another therapeutic area where embodiments of the present disclosure may be applicable is inhibiting the process of restenosis. Restenosis is the result of a complex process involving inflammation and proliferation activated by a response to a percutaneous or surgical vascular intervention. Examples of these percutaneous or surgical interventions may include, but are not limited to, the revascularization of vascular bypass grafts, arteriovenous fistulas, arteriovenous grafts and percutaneous revascularization of coronary, femoral, and carotid vessels. Atherosclerotic plaque arising from the arterial wall can reduce cross-sectional flow area which limits flow to downstream organs. Cross-sectional flow area can be restored by displacing (e.g. using an expandable balloon or stent) or removing the lesion (e.g. directional or rotational atherectomy). In the months to weeks after revascularization, local proliferative of arterial wall smooth muscle cells can create an obstruction to flow at the site of the original atherosclerotic plaque.

Pulmonary Disease

Another therapeutic area where embodiments of the present disclosure could be applicable is a luminal surface of normal or diseased airways for the treatment or prevention of focal diseases of the lung and airways. This embodiment may be used in conjunction with both a rigid and/or flexible bronchoscope, which are commonly used to facilitate access to and visualization of the target treatment area.

In general, focal diseases of the airways include neoplasms that are categorized as either benign or malignant. Primary neoplasms may be classified as epithelial, mesenchymal or lymphoid tumors; more than 20 types of tracheal neoplasms have been described.

Carcinoid tumors represent approximately 85 percent of adenomas of the tracheobronchial tree. Adenoid cystic carcinoma is the most frequent adenoma of the trachea. Adenoid cystic carcinoma (or cylindroma) is the second most common malignancy and also the second most common primary tracheal neoplasm.

Depending upon the specific neoplasm type and behavior as well as the time of diagnosis, the neoplasm may or may not present a physical obstruction or protrusion into the lumen of the airways. It is envisioned that an approach to restoring functional luminal patency could be to mechanically restore luminal patency by displacing the tumor with a balloon or reduce tumor bulk and then locally delivering a drug to inhibit tumor growth and/or tumor survival. Local drug delivery using embodiments of the present disclosure could be an effective method of delivering chemotherapeutic agents effective against benign or malignant neoplasms to the luminal aspect of the tumor. Specifically, embodiments of the present disclosure could be applied to a catheter or a bronchoscope and advanced antegradely or retrogradely to the intended site of local drug delivery.

Gastrointestinal Disease

Another therapeutic area where embodiments of the present disclosure could be applicable includes the treatment of gastrointestinal diseases such as, but not limited to, benign and malignant tumors of the esophagus, biliary tract, colon, and small bowel.

Esophageal tumors are caused by dysregulated division of esophageal smooth muscle or epithelial cells. The tumors can be either benign (e.g. leiomyoma) or malignant (squamous cell carcinoma or adenocarcinoma). These tumors can grow into the lumen and compromise the functional cross-sectional area of the esophagus causing dysphagia (abnormal swallowing) and consequent malnutrition.

It is envisioned that an approach to restoring functional lumenal patency could be to mechanically restore luminal patency by displacing the tumor with a balloon or metal dilator or reduce tumor bulk (e.g. laser ablation), and then locally delivering a therapeutic agent to inhibit tumor growth and/or tumor survival. Local therapeutic agent delivery using embodiments of the present disclosure could be an effective method for delivering chemotherapeutic agents that are effective against benign or malignant esophageal tumors to the luminal aspect of the tumor. Specifically, embodiments of the present disclosure could be applied to a catheter or an endoscope and advanced antegradely or retrogradely to the intended site of local drug delivery.

A similar approach could be used with malignancies of the biliary tract. Cholangiocarcinoma is the most common biliary tract malignancy. It is caused by dysregulated division of cholangiocytes. These tumors can compromise the functional lumen of the intra- or extra-hepatic biliary tree causing cholestasis and consequent cholangitis, pruritis, fat malabsorption, and anorexia.

It is envisioned that an approach to restoring functional lumenal patency could be to mechanically restore luminal patency by displacing the tumor with a balloon, blade, or metal dilator, or reduce tumor bulk (e.g. laser ablation), and then locally deliver a therapeutic agent to inhibit tumor growth and/or tumor survival utilizing embodiments of the present disclosure.

Approaches similar to that described above for esophageal and biliary tract malignancies could be developed for small bowel and colonic malignancies. Analogous approaches could also be used to locally delivery therapeutic agents to treat non-malignant gastrointestinal diseases (e.g. anti-inflammatory agents delivered to treat inflammatory bowel disease). Therapeutic agents for the above indication that exhibit water-only solubility or require water for solubilization, such as carboplatin, cisplatin, the epothilones, interferons (interferon-alpha) and targeted proteins such as antibodies (such as the EGFR inhibitor cetuximab), can be formulated into the disclosed amphiphilic polymer coating by the use of water as part or all of the solvent system.

Advantages of the balloons of the present disclosure include, but are not limited to, the following.

Reduced Toxicity: Paclitaxel is a cytotoxic drug; coatings of the present disclosure have low levels of paclitaxel and therefore the maximum systemic exposure is significantly reduced.

First Line Treatment: The thinner, more durable, coatings of the present disclosure might be used as a first line of treatment device and negate the need for pre-dilatation.

Lower Profile: Thinner coatings by definition have a smaller profile. This will allow for better maneuverability inside the vessel.

A More Dilute Coating Formulation: The lower viscosity will improve the uniformity of the coating on the balloon, both in terms of longitudinal uniformity and content uniformity within a device lot.

Improved Coating Integrity: Thinner coatings generally have better coating integrity because the coating acts less like a singular film and more like individual smaller pieces. Thus, expansions and stresses are less likely to fragment the coating, resulting in more coating reaching the treatment site.

Enhanced Delivery: Even though coatings of the present disclosure are thinner than conventional coatings, they are capable of delivering comparable amounts of therapeutic agents in vivo.

More Economical: Coatings of the present disclosure require less drug, and thus may be more economical to produce.

Multiple Deployments: Coatings of the present disclosure are capable of delivering therapeutic agents in amounts comparable to conventional devices, even after repeated uses/deployments.

Several embodiments of the disclosure are described below with reference to the following non-limiting Examples regarding coating of balloons. Solution percentages provided are by weight.

COMPARATIVE EXAMPLE 1

Preparation of Coating Solution. The coating solution included a mixture of paclitaxel, a low molecular weight polyethylene glycol polymer (8 kDa PEG) and molecular iodine ($I_2$). The polymer, iodine and paclitaxel were combined with an azeotrope solution that included 57% ethanol and 43% acetonitrile. The materials were mixed for approximately 5 minutes at 42° C. in order to fully dissolve all the components. The coating solution may be stored in a refrigerator at 5° C. for up to one week prior to use.

EVERCROSS™ 0.035" and NANOCROSS™ 4×40 mm balloon catheters, commercially available from Covidien, were used for all coatings. Briefly, the balloon catheters were coated as follows. The balloon catheter was removed from its packaging, the protector sheath removed, and the balloon inflated with air to approximately 3 atmospheres. Optionally the balloon catheter was pre-conditioned (cleaned using isopropyl alcohol followed by air drying and/or Argon-plasma treated). The balloon catheter was dip-coated into the above coating solution at 70° F. at an angle of 90° to a nominal paclitaxel dose of 2.0 µg/mm². The balloon catheter was rotated at 58±2 rpm during the coating process. The coated balloon was dried for between 5 minutes and 24 hours. After drying, the coated balloon catheter was post-processed by dipping into deionized water at 70° F. at an angle of 90°. The balloon catheter was not rotated during the post-processing dip. The post-processed balloon catheter was allowed to dry for between 1 hour and 24 hours, the balloon was then inspected, folded, sheathed and sterilized using ethylene oxide. These balloons were referred to as Control.

EXAMPLE 1

Briefly the balloon catheters were coated as follows. The balloon catheter was removed from its packaging, the protector sheath removed, and the balloon inflated with air to approximately 3 atmospheres. Optionally the balloon catheter was pre-conditioned (cleaned using isopropyl alcohol followed by air drying and/or Argon-plasma treated). The balloon catheter was dip-coated into the coating solution at 70° F. at an angle of 90° to a nominal paclitaxel dose set forth below in Table 1. The balloon catheter was rotated at 58±2 rpm during the coating process. The balloon catheters were allowed to dry for between 5 minutes and 24 hours. The balloon was then inspected, folded, sheathed and sterilized using ethylene oxide.

Coating formulations of the present disclosure were prepared following the methods described above. Serial dilutions of the "A" coating solution with the solvents (azeotrope) were performed to generate the "B-D" formulations (See Table 1 below).

The concentration of each component (paclitaxel, PEG & $I_2$) is given in Table 1 for each of the twelve coating formulations of this Example and the Control from Comparative Example 1 above.

TABLE 1

| | | | Formulation Matrix | | | | | |
|---|---|---|---|---|---|---|---|---|
| Coating # | paclitaxel Target (µg/mm²) | paclitaxel (mg/mL) | paclitaxel (wt %) | PEG (mg/mL) | PEG (wt %) | $I_2$ (mg/mL) | $I_2$ (wt %) | Total mg/mL |
| 1A | 0.6 | 61.5 | 70 | 22.0 | 25 | 4.5 | 5 | 88.0 |
| 1B | 0.4 | 39.4 | 70 | 14.1 | 25 | 2.9 | 5 | 56.3 |
| 1C | 0.2 | 20.5 | 70 | 7.3 | 25 | 1.5 | 5 | 29.3 |
| 1D | 0.1 | 10.6 | 70 | 3.8 | 25 | 0.8 | 5 | 15.2 |
| 2A | 0.6 | 61.5 | 60 | 36.0 | 35 | 5.0 | 5 | 102.5 |
| 2B | 0.4 | 39.4 | 60 | 23.0 | 35 | 3.2 | 5 | 65.6 |
| 2C | 0.2 | 19.7 | 60 | 11.5 | 35 | 1.6 | 5 | 32.8 |
| 2D | 0.1 | 9.8 | 60 | 5.8 | 35 | 0.8 | 5 | 16.4 |
| 3A | 0.6 | 61.5 | 50 | 55.0 | 45 | 6.0 | 5 | 122.5 |
| 3B | 0.4 | 39.4 | 50 | 35.2 | 45 | 3.8 | 5 | 78.4 |
| 3C | 0.2 | 19.7 | 50 | 17.6 | 45 | 1.9 | 5 | 39.2 |

TABLE 1-continued

Formulation Matrix

| Coating # | paclitaxel Target (µg/mm²) | paclitaxel (mg/mL) | paclitaxel (wt %) | PEG (mg/mL) | PEG (wt %) | $I_2$ (mg/mL) | $I_2$ (wt %) | Total mg/mL |
|---|---|---|---|---|---|---|---|---|
| 3D | 0.1 | 9.8 | 50 | 8.8 | 45 | 1.0 | 5 | 19.6 |
| Control | 2.0 | 61.5 | na* | 145.8 | na* | 6.8 | na* | 214.1 |

*Weight percent changed significantly due to post-processing.

The above formulations were coated onto 4×40 mm balloons, following the same general procedures described above for the control balloons in Comparative Example 1.

Twenty-four (24) Device Lots were manufactured, the details of which are summarized below in Table 2. Balloons on both 5 French (5 Fr.) and 6 French (6 Fr.) catheters were coated.

The Total Drug Content (TDC) (n=1) was determined spectroscopically at the wavelength of maximum absorbance ($\lambda_{max}$=228 nm) in Methanol (MeOH) extracts as set forth below in Table 2.

TABLE 2

Coating Matrix

| # | Coating | Sheath Size | paclitaxel Target (µg/mm²) | Target TDC (µg) | paclitaxel Measured (µg/mm²) | Measured TDC (µg) | paclitaxel: PEG:$I_2$ |
|---|---|---|---|---|---|---|---|
| 1 | 1A | 5 Fr | 0.60 | 385 | 0.65 | 415 | 70:25:5 |
| 2 | 1B | | 0.40 | 257 | 0.36 | 232 | |
| 3 | 1C | | 0.20 | 128 | 0.18 | 114 | |
| 4 | 1D | | 0.10 | 64 | 0.09 | 57 | |
| 5 | 2A | | 0.60 | 385 | 0.72 | 463 | 60:35:5 |
| 6 | 2B | | 0.40 | 257 | 0.39 | 253 | |
| 7 | 2C | | 0.20 | 128 | 0.18 | 115 | |
| 8 | 2D | | 0.10 | 64 | 0.09 | 56 | |
| 9 | 3A | | 0.60 | 385 | 0.68 | 436 | 50:45:5 |
| 10 | 3B | | 0.40 | 257 | 0.35 | 222 | |
| 11 | 3C | | 0.20 | 128 | 0.15 | 96 | |
| 12 | 3D | | 0.10 | 64 | 0.08 | 50 | |
| 13 | 1A | 6 Fr | 0.60 | 385 | 0.68 | 436 | 70:25:5 |
| 14 | 1B | | 0.40 | 257 | 0.40 | 256 | |
| 15 | 1C | | 0.20 | 128 | 0.19 | 120 | |
| 16 | 1D | | 0.10 | 64 | 0.09 | 58 | |
| 17 | 2A | | 0.60 | 385 | 0.82 | 526 | 60:35:5 |
| 18 | 2B | | 0.40 | 257 | 0.43 | 276 | |
| 19 | 2C | | 0.20 | 128 | 0.19 | 119 | |
| 20 | 2D | | 0.10 | 64 | 0.09 | 56 | |
| 21 | 3A | | 0.60 | 385 | 0.71 | 457 | 50:45:5 |
| 22 | 3B | | 0.40 | 257 | 0.36 | 230 | |
| 23 | 3C | | 0.20 | 128 | 0.16 | 100 | |
| 24 | 3D | | 0.10 | 64 | 0.07 | 47 | |
| 25 | Control | | 2.00 | 1284 | 2.09 | 1340 | 70:25:5 |

Delivery of paclitaxel to arterial tissue with the balloons from Comparative Example 1 and the above balloons was determined as follows.

Tissue deployments were performed on a bench model using ovine or porcine carotid and internal mammary arterial tissue (Ø ~4 mm). The source animals were not used for any pharmaceutical investigation. The tissue was sectioned into lengths of approximately 45 mm. Excess fat and adventitia were removed using surgical tools.

Tissue was stored in either phosphate-buffered saline (PBS) or RPMI cell culture media in a refrigerator. If the tissue was stored in PBS, it was only be used in the bench model for up to three (3) days from the harvest time. If the tissue was stored in RPMI, it was only used for up to seven (7) days from the harvest time.

The bench model included a tube in which the arterial tissue was placed, coupled to tubing which permitted the flow of fluids there through.

After the tissue was mounted onto the bench model, fetal bovine serum (FBS) was pumped through the model at ~80 mL/min.

A balloon was then inserted into the model such that, at a minimum, the working length of the balloon would be in direct contact with the tissue at nominal inflation pressure (NIP).

The balloon was inflated in the tissue for 1 minute at nominal inflation pressure (NIP), in this case, 10 atmospheres, and then the balloon was deflated and removed.

Serum was pumped for an additional minute before the flow was stopped to remove any large coating pieces that may have given erroneous data if analyzed.

The tissue segment was the removed and measured for paclitaxel content using an LCMS method by an outside vendor, BASi Corporation, McMinnville, Oreg.

The balloons were briefly washed in water and saved for later post-deployment TDC analysis.

Balloons that had been deployed were inserted into an appropriate amount of MeOH (10 mL for "A" coatings, 5 mL for "B", "C", and "D" coatings).

After sonication, aliquots of the solution were placed into 1 mL centrifuge tubes.

The tubes were centrifuged for 2 minutes at 14,000 RPM.

The supernatant of each sample was then analyzed and the amount of PTX remaining on the balloon was determined spectroscopically.

The Total Drug Content (TDC) of residual drug on balloons after deployment is set forth below in Table 3.

TABLE 3

Residual Drug TDC Results for the twenty-four (24) coated lots.

| Coating# | 5 Fr-Average paclitaxel % Recovery | 6 Fr-Average paclitaxel % Recovery |
|---|---|---|
| 1A | 69 (n = 5) | 35 (n = 3) |
| 2A | 45 (n = 5) | 22 (n = 2) |
| 3A | 64 (n = 5) | 21 (n = 4) |
| 3B | 62 (n = 5) | 16 (n = 4) |
| Control | Na | 25 (n = 5) |

Coatings were ranked based on paclitaxel uptake and uniformity of uptake (that is, higher paclitaxel values along with lower standard deviation values). Table 4 below shows the acute uptake of five (5) selected coatings with preferable combinations of these two factors.

TABLE 4

Selected Coatings

Paclitaxel (µg) Uptake in 40 mm length of Tissue

|   | Control | 3A (5 Fr) | 3B (5 Fr) | 1A (6 Fr) | 2A (6 Fr) | 3B (6 Fr) |
|---|---|---|---|---|---|---|
| 1 | 12.6 | 4.6 | 7.6 | 5.9 | 3.6 | 11.7 |
| 2 | 19.5 | 15.7 | 18.3 | 28.9 | 10.4 | 9.0 |
| 3 | 28.9 | 9.7 | 9.1 | 10.5 | 19.2 | 10.7 |
| 4 | 32.4 | 8.5 | 9.9 | 17.0 | 5.1 | 6.2 |
| 5 | 9.1 | 11.5 | 7.4 | na | na | na |
| Average | 20.5 | 10.0 | 10.5 | 15.6 | 9.6 | 9.4 |
| Standard deviation | 10.0 | 4.1 | 4.5 | 10.0 | 7.0 | 2.4 |
| % RSD | 49.0 | 40.5 | 43.0 | 64.2 | 73.2 | 25.4 |

RSD = relative standard deviation

For the control balloon, some of the paclitaxel payload was transferred to the artery; this was an inefficient process wherein approximately 1-2% of the total payload of paclitaxel on the balloon was transferred to the artery. This 1-2% transfer of paclitaxel from the balloon, with a dose density of 2 µg/mm$^2$, was sufficient to deliver enough paclitaxel to the artery.

EXAMPLE 2

Covidien/ev3 NANOCROSS™ 0.014" balloon catheters (4×40 mm) were used in this study.

The balloons were dip-coated into the 3B coating formulation noted above.

The effect of plasma treatment, balloon cleaning, humidification, and Fr. size on coating appearance, integrity and acute paclitaxel uptake into porcine carotid tissues on the bench model described above in Example 1 were evaluated.

Devices were divided into eight (8) groups (See Table 5 below for Sample Matrix).

Fifty eight (58) devices were evaluated wherein the following parameters were varied:

Small 3.5 (Fr) vs. Large 4.5 (Fr) Balloon Protector Sheaths;

IPA cleaned+60 seconds sonication vs. Not Cleaned Balloons;

120 seconds vs. 30 seconds Plasma Treatment;

Humidified vs. Non-Humidified; and

Single Deployment vs. Multiple Deployments.

Groups A, B, E, and F were cleaned in 99.5% IPA with 60 seconds sonication (See Sample Matrix in Table 5 below).

Groups C, D, G, and H were not cleaned (See Sample Matrix in Table 5 below).

After cleaning, the balloons were blown off with compressed air and allowed to air dry for at least one (1) hour.

Balloons were masked with a silicone mask placed over the tip of the balloon to cover up to the distal marker band; balloon was inflated with air using a 10 mL plastic syringe to approximately 3 atm.

TABLE 5

Sample Matrix

| Sheath Sizes | Group | 60 sec IPA Cleaning | Plasma (sec) | Humidify | 1x Deployment | 3x Deployment |
|---|---|---|---|---|---|---|
| Small 3.5 (Fr) | A | Yes | 120 | Yes | 3 | 3 |
|  | B |  |  | No | 3 | 3 |
|  | C | No | 30 | Yes | 3 | n/a |
|  | D |  |  | No | 3 | n/a |
| Large 4.5 (Fr) | E | Yes | 120 | Yes | 3 | n/a |
|  | F |  |  | No | 3 | n/a |
|  | G | No | 30 | Yes | 3 | n/a |
|  | H |  |  | No | 3 | n/a |

Residual paclitaxel on the balloon (Post Tissue TDC) was analyzed using a UV-vis Spectrophotometer.

Thirty (30) sterile devices were deployed into porcine carotid tissue on the Bench Model described above in Example 1 and the amount of paclitaxel acutely transferred to the tissue was determined using LCMS as described above in Example 1.

Two (2) sterile-humidified devices were analyzed for Characterization of the paclitaxel in the balloon with 1% SDS.

The 3B coatings retained a much higher % of paclitaxel on the balloon after tissue deployment compared to the control coatings of Comparative Example 1 (2.0 µg/mm$^2$, EVERCROSS™ platform).

All groups demonstrated comparable tissue uptake for paclitaxel with respect to the control.

The acute paclitaxel uptake was not significantly affected by:

Balloon cleaning in IPA (no clean vs. 60 sec in IPA with sonication);

Plasma Treatment (30 sec vs. 120 sec in plasma chamber);

Balloon Protective Sheaths (BPS) size (3.5 Fr. vs. 4.5 Fr.);

Single Deployment (1×) vs. Multiple Deployment (3×); and

Post-processing Humidification (no humidity vs. humidification).

The average amount of paclitaxel delivered to tissue for each group is reported in Table 6 below.

TABLE 6

Paclitaxel (µg) Amount in Tissue

| Group | BPS Size | Cleaning/ Plasma | Humidified | Deployment | Average Paclitaxel (µg) | Average Paclitaxel (µg/mm length of tissue) | % Paclitaxel (as % of coating) |
|---|---|---|---|---|---|---|---|
| A1x | 3.5 Fr | IPA, 120 sec plasma | Yes | 1X | 20.7 ± 11.5 | 0.5 ± 0.3 | 8.2 ± 4.6 |
| A3x | | | | 3X | 24.1 ± 9.3 | 0.6 ± 0.2 | 9.6 ± 3.7 |
| B1x | | | No | 1X | 14.5 ± 9.5 | 0.4 ± 0.2 | 5.8 ± 3.8 |
| B3x | | | | 3X | 27.4 ± 13.3 | 0.7 ± 0.3 | 10.9 ± 5.3 |
| C | | no IPA, 30 sec plasma | Yes | 1X | 27.9 ± 10.4 | 0.7 ± 0.3 | 11.1 ± 4.1 |
| D | | | No | 1X | 15.5 ± 7.8 | 0.4 ± 0.2 | 6.2 ± 3.1 |
| E | 4.5 Fr | IPA, 120 sec plasma | Yes | 1X | 23.7 ± 7.6 | 0.6 ± 0.2 | 9.4 ± 3.0 |
| F | | | No | 1X | 24.0 ± 3.2 | 0.6 ± 0.1 | 9.5 ± 1.3 |
| G | | no IPA, 30 sec plasma | Yes | 1X | 26.0 ± 6.0 | 0.6 ± 0.2 | 10.3 ± 2.4 |
| H | | | No | 1X | 20.9 ± 8.4 | 0.5 ± 0.2 | 8.3 ± 3.4 |
| Control | 6 Fr | n/a | No | 1x | 20.5 ± 10.0 | 0.5 ± 0.3 | 1.5 ± 0.7 |

The residual (%) paclitaxel remaining on the balloons after deployment is reported in Table 7 below.

TABLE 7

Paclitaxel (%) Remaining on the Balloons

| Group | BPS Size | Cleaning/Plasma | Humidified | Deployment | % paclitaxel |
|---|---|---|---|---|---|
| A1x | 3.5 Fr | IPA, 120 sec plasma | Yes | 1X | 36% ± 23% |
| A3x | | | | 3X | 2% ± 6% |
| B1x | | | No | 1X | 25% ± 9% |
| B3x | | | | 3X | 17% ± 8% |
| C | | no IPA, 30 sec plasma | Yes | 1X | 26% ± 2% |
| D | | | No | 1X | 25% ± 6% |
| E | 4.5 Fr | no IPA, 30 sec plasma | Yes | 1X | 48% ± 21% |
| F | | | No | 1X | 32% ± 5% |
| G | | no IPA, 30 sec plasma | Yes | 1X | 37% ± 4% |
| H | | | No | 1X | 14% ± 4% |
| Control | 6 | n/a | No | 1x | 25% ± 5% |

The thinner (3B) coated balloons in general achieved a higher % residual paclitaxel remaining on the balloons than the corresponding 2.0 µg/mm² coatings.

The 3B coated balloons demonstrated an excellent coating uniformity and integrity.

Figure 3:
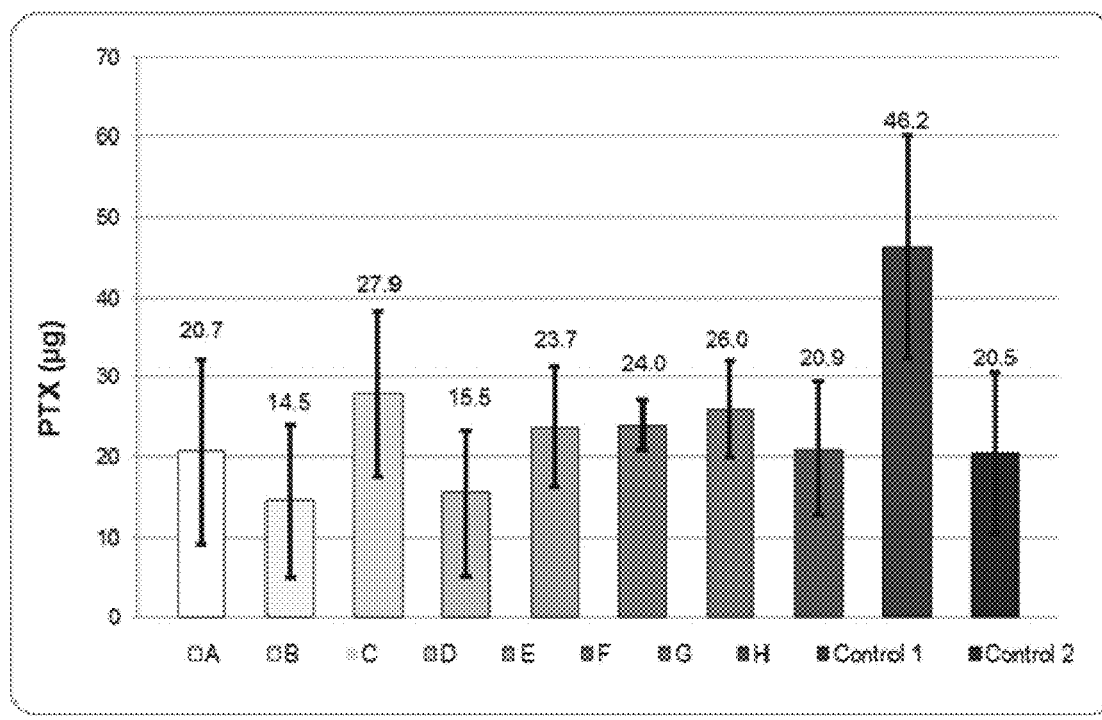
FIG. 3 is a graph depicting average uptake values for a single deployment of a balloon coated with paclitaxel in accordance with the present disclosure.

The average uptake values for single deployment are plotted on FIG. 3.

Figure 4:
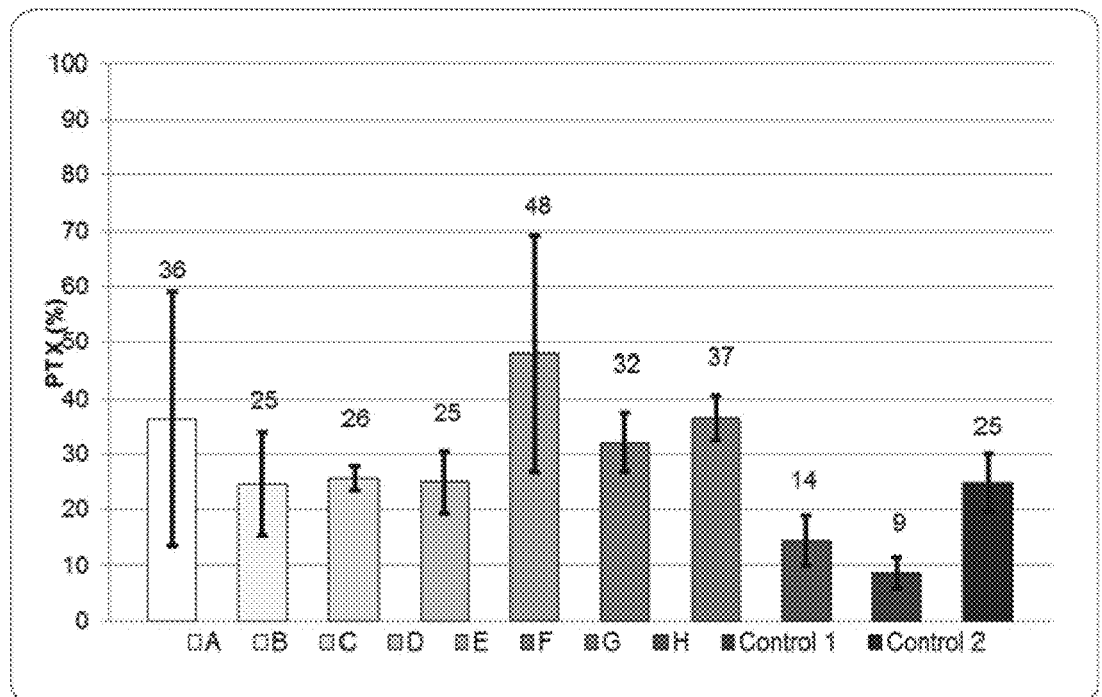
FIG. 4 is a graph depicting residual paclitaxel (%) on a balloon coated in accordance with the present disclosure after a single deployment.

FIG. 4 shows the % paclitaxel remaining on the balloon.

Figure 5:
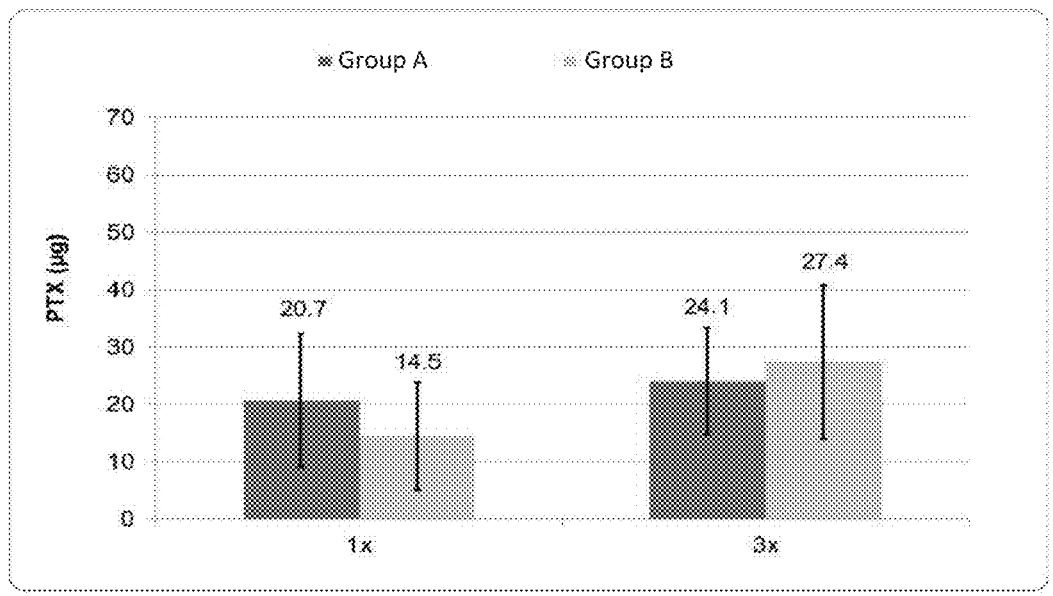
FIG. 5 is a graph comparing average tissue uptake values for the single deployment of control balloons compared with multiple deployments of balloons coated with paclitaxel in accordance with the present disclosure.

The average tissue uptake values for single vs. multiple deployments of the Control balloons and 3B balloons are plotted on FIG. 5.

Figure 6:
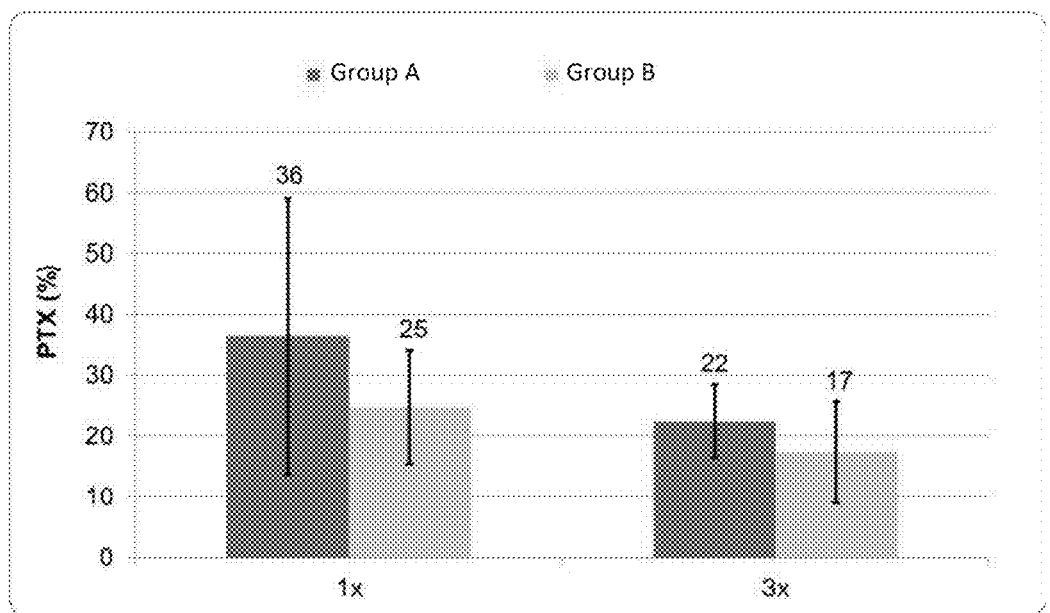
FIG. 6 is a graph depicting paclitaxel (%) deployed from balloons coated in accordance with the present disclosure compared with control balloons after single and multiple deployments.

The amount of paclitaxel (%) deployed from 3B balloons compared with balloons from Comparative Example 1a after multiple deployments are set forth in FIG. 6.

Figure 7:
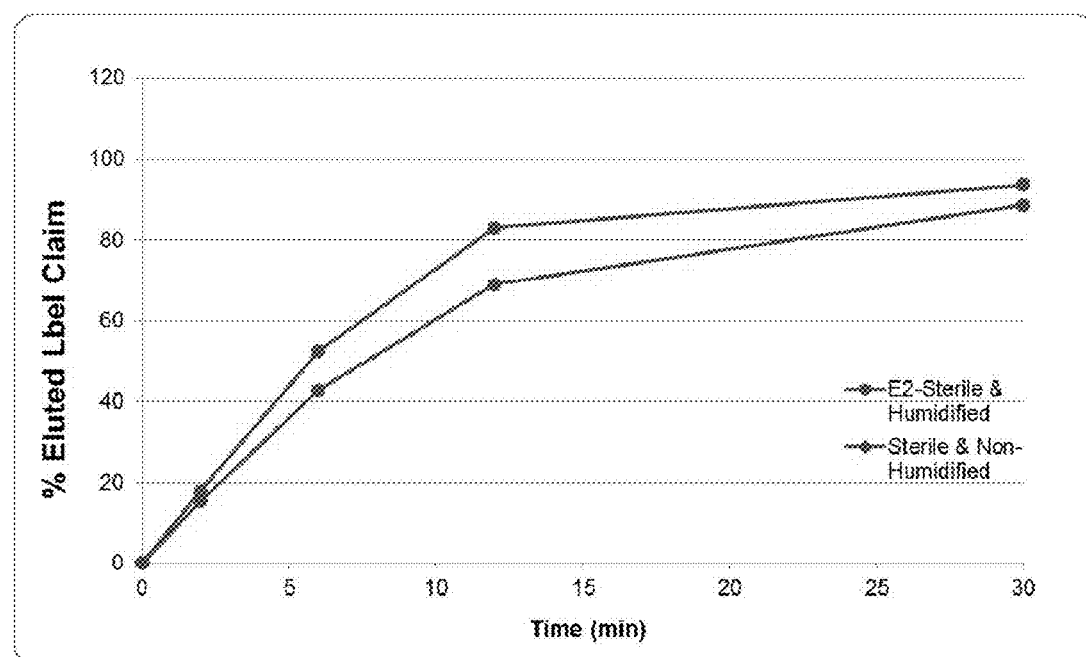
FIG. 7 is a graph comparing the effects humidity had on the elution profiles of balloons coated in accordance with the present disclosure.

Two (2) devices were eluted in 1% SDS to characterize the coating. Both devices eluted to greater than 80% of nominal at 30 minutes (see FIG. 7 (in FIG. 7, E2=Sterile & Humidified, and F5=Sterile & Non-humidified)).

Groups that were humidified with IPA+60 second sonication and 120 seconds plasma treatment appeared to have an excellent coating appearance and very good coating integrity.

Groups that were non-humidified with no cleaning and 30 seconds plasma treatment showed non-uniform coating appearance and poor coating integrity.

Confocal Raman spectroscopy was performed on an amorphous paclitaxel standard and a dihydrate paclitaxel standard. Balloons produced in accordance with the present disclosure were then subjected to Confocal Raman spectroscopy and compared with the spectra for the standards. It was observed that the balloons produced in accordance with the present disclosure possessed dihydrate paclitaxel thereon.

The coatings of the present disclosure were successfully manufactured at the targeted doses.

The average amount of paclitaxel delivered to tissue via single deployment is reported in Table 8 below.

The average amount of paclitaxel delivered to tissue via multiple (3x) arteries deployment is reported in Table 9 below.

Multiple arteries (3x) deployment data demonstrated that the coated balloons could deliver adequate amount of paclitaxel to tissues in second or even third deployment.

Humidified balloons (Group D) had a better paclitaxel tissue uptake in second and third deployments compared to non-humidified balloons (Group C.)

TABLE 8

Paclitaxel Tissue Uptake – Single Deployment (n = 5)

| Group | Description | Paclitaxel (µg) | Paclitaxel (%) |
|---|---|---|---|
| A | Freshly coated | 7.3 ± 5.3 | 3.2 ± 2.4 |
| B | Humidified, non-sterile | 17.4 ± 6.5 | 7.7 ± 2.9 |
| C | Non-Humidified, Sterile | 26.6 ± 12.1 | 11.8 ± 5.4 |
| D | Humidified, Sterile | 22.4 ± 5.6 | 10.0 ± 2.5 |

TABLE 9

Paclitaxel Tissue Uptake – Multiple Arteries (3x) Deployments (n = 3)

| Group | Description | Deployment | paclitaxel (µg) | paclitaxel (%) |
|---|---|---|---|---|
| C | Non-Humidified, Sterile | 1st | 20.8 ± 17.1 | 9.3 ± 7.6 |
| | | 2nd | 4.2 ± 0.9 | 1.9 ± 0.4 |
| | | 3rd | 3.3 ± 2.9 | 1.5 ± 1.3 |
| D | Humidified, Sterile | 1st | 15.2 ± 1.7 | 6.8 ± 0.8 |
| | | 2nd | 12.2 ± 3.1 | 5.4 ± 1.4 |
| | | 3rd | 8.5 ± 2.4 | 3.8 ± 1.1 |

The residual (%) paclitaxel remaining on the balloons after deployment is reported in Table 10.

Table 10

| | Paclitaxel Remaining on the Balloons | | | |
|---|---|---|---|---|
| Group | Description | Deployment | Residual paclitaxel (μg) | Residual paclitaxel (%) |
| A | Freshly coated | 1x | 153.3 ± 14.5 | 68 ± 6 |
| B | Humidified, non-sterile | 1x | 119.2 ± 35.1 | 53 ± 16 |
| C | Non-Humidified, Sterile | 1x | 86.7 ± 31.8 | 39 ± 14 |
| | | 3x | 16.0 ± 8.1 | 7 ± 4 |
| D | Humidified, Sterile | 1x | 106.9 ± 28.7 | 47 ± 13 |
| | | 3x | 54.2 ± 10.4 | 24 ± 5 |

The DCB was mounted on a catheter, packaged, and sterilized with ethylene oxide.

The nominal concentration of paclitaxel on the 3B coated balloon was 0.42 μg/mm$^2$, the nominal ratio of paclitaxel: PEG:I$_2$ was approximately 50:45:5.

In the foregoing specification, various embodiments of the disclosure have been described. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A catheter assembly for insertion into the vasculature comprising:
    a balloon having an outer surface; and
    a coating disposed on the outer surface of the balloon, wherein the coating comprises;
        an amphiphilic polymer matrix;
        a therapeutic agent dispersed throughout the polymer matrix; and
        iodine,
    wherein a ratio of the amphiphilic polymer matrix to the therapeutic agent to the iodine is about 50:45:5 to about 70:25:5,
    wherein the coating has a thickness from about 0.01 μm to about 10 μm and a therapeutic agent density of from about 0.1 μg/mm$^2$ to about 1.5 μg/mm$^2$.

2. The catheter assembly of claim 1, wherein the polymer matrix comprises a polymer selected from the group consisting of polyethylene glycol, polyvinyl pyrrolidone and hydroxypropyl cellulose.

3. The catheter assembly of claim 1, wherein the therapeutic agent is paclitaxel.

4. The catheter assembly of claim 1, wherein the polymer matrix comprises polyethylene glycol.

5. The catheter assembly of claim 4, wherein the polyethylene glycol has a molecular weight of 1.5 KD to 50 KD.

6. The catheter assembly of claim 1, wherein the coating has a therapeutic agent density of from about 0.25 μg/mm$^2$ to about 0.8 μg/mm$^2$.

7. A catheter assembly for insertion into the vasculature comprising:
    a balloon having an outer surface;
    an amphiphilic coating comprising:
        a polymer matrix complexed with iodine disposed on the outer surface of the balloon; and
        a therapeutic agent dispersed in the matrix complexed with the iodine,
    wherein a ratio of the polymer matrix to the therapeutic agent to the iodine is about 50:45:5 to about 70:25:5,
    wherein the amphiphilic coating has a thickness from about 0.01 μm to about 10 μm and a therapeutic agent density of from about 0.1 μg/mm$^2$ to about 1.5 μg/mm$^2$.

8. The catheter assembly of claim 7, wherein the iodine is complexed with polyethylene glycol, polyvinyl pyrrolidone, or hydroxypropyl cellulose.

9. The catheter assembly of claim 7, wherein the therapeutic agent is paclitaxel.

10. The catheter assembly of claim 7, wherein the polymer matrix comprises polyethylene glycol.

11. The catheter assembly of claim 10, wherein the polyethylene glycol has a molecular weight of 1.5 KD to 50 KD.

12. The catheter assembly of claim 7, wherein the coating has a therapeutic agent density of from about 0.25 μg/mm$^2$ to about 0.8 μg/mm$^2$.

13. A catheter assembly for insertion into the vasculature comprising:
    a balloon having an outer surface;
    an amphiphilic coating disposed on the outer surface of the balloon, the amphiphilic coating comprising:
        polyethylene glycol
        a therapeutic agent comprising paclitaxel dispersed throughout the polyethylene glycol; and
        iodine,
    wherein a ratio of the polymer matrix to the therapeutic to the iodine is about 50:45:5 to about 70:25:5,
    wherein the amphiphilic coating has a therapeutic agent density of from about 0.1 μg/mm$^2$ to about 1.5 μg/mm$^2$, and
    wherein the amphiphilic coating has a thickness from about 0.01 μm to about 10 μm.

14. The catheter assembly of claim 1, wherein the polymer matrix comprises at least one amphiphilic polymer.

15. The catheter assembly of claim 1, wherein the polymer matrix comprises at least one amphiphilic copolymer.

16. The catheter assembly of claim 7, wherein the polymer matrix comprises at least one amphiphilic polymer.

17. The catheter assembly of claim 7, wherein the polymer matrix comprises at least one amphiphilic copolymer.

* * * * *